US005311841A

United States Patent [19]
Thaxton

[11] Patent Number: 5,311,841

[45] Date of Patent: May 17, 1994

[54] ADMINISTRATION OF MEDICAMENTS OF POULTRY

[76] Inventor: J. Paul Thaxton, 117 Campfire Cir., Brandon, Miss. 39042

[21] Appl. No.: 911,972

[22] Filed: Jul. 10, 1992

[51] Int. Cl.[5] .......... A61M 31/00

[52] U.S. Cl. .......... 604/51; 604/144; 119/174

[58] Field of Search .......... 119/174, 6.8, 103; 426/2; 604/117, 144, 47, 46, 49, 51; 128/898

[56] References Cited

U.S. PATENT DOCUMENTS

| | | | |
|---|---|---|---|
| 2,824,546 | 2/1958 | Klette | 119/6.8 |
| 4,108,176 | 8/1978 | Walden | 604/144 |
| 4,177,810 | 12/1979 | Gourlandt | 604/144 |
| 4,458,630 | 7/1984 | Sharma et al. | 119/6.8 |
| 4,604,968 | 8/1986 | Christensen . | |
| 4,681,063 | 7/1987 | Hebrank . | |
| 4,903,635 | 2/1990 | Hebrank . | |
| 4,935,007 | 6/1990 | Bafundo et al. | 604/49 |

OTHER PUBLICATIONS

C. R. Parkhurst, et al, Chapter 5, "Incubation and Hatchery Management," in Poultry Meat and Egg Production, Van Nostrand (New York) (1989).

Whiteman, C. E., et al, "*Coccidiosis*", Avian Disease Manual, Kendall/Hunt Publishing Co., pp. 153–157, (1989).

Long, P. L., et al., Exp. Parasitol, 16:1–7 (1965).

Sharma, N. N., et al, J. Parasitol, 50:509–517 (1964).

Rose, M. E., et al, Parasitol, 102:317–324 (1990).

Jeurissen, et al., Develop. and Comp. Immunol., 15:437–442 (1991).

"The ViMark Pneumatic Vaccinator Instruction Manual", Vineland Laboratories, Inc.

Hofmann, et al, Parasitol, 76:479–486 (1990).

*Primary Examiner*—John G. Weiss

[57] ABSTRACT

A method for the delivery of medicaments to newly hatched poultry. A vaccine or other medicament is injected into the yolk sac of a newly hatched chick, and is released to the chick's system as the yolk is absorbed by the chick. An injection device is shown having one or optionally a pair of guide services for guiding a chick axially of a hypodermic needle during an injection procedure to reduce damage to the injection site.

11 Claims, 6 Drawing Sheets

ADMINISTRATION OF MEDICAMENTS OF POULTRY

TECHNICAL FIELD

The present invention relates to methods for the delivery of medicaments, such as vaccines, to domestically raised poultry.

BACKGROUND OF THE INVENTION

Domestically raised poultry, such as chickens, turkeys, ducks, geese, guineas, pheasants, and quail, are subject to a variety of diseases and infections after hatching. Some resistance to disease is provided by naturally-occurring antibodies and virus-neutralizing gamma globulins in the yolk of the egg, which is carried by the chick immediately beneath the skin of the abdomen. The yolk contents are absorbed into the digestive tract of the chick over a seven to nine day period after hatching. See, e.g., C. R. Parkhurst and G. J. Mountney (1989), Chapter 5, "Incubation and Hatchery Management," in Poultry Meat and Egg Production, Van Nostrand (New York), the disclosure of which is incorporated herein by reference.

Supplementary medications can be administered to poultry by several methods, including subcutaneous injection and eye drops. Subcutaneous injections commonly are performed in the necks of newly hatched chicks on an assembly line basis, and equipment for this purpose is available commercially. In this procedure, the chicks are manually picked up one by one and their necks are placed against an automatic injection device; an injection needle is quickly advanced into the chick's neck, a measured dose of medication is injected, and the needle is withdrawn. The medication injected in this manner diffuses rapidly into the chick's vascular system.

In an effort to provide poultry with a measure of immunity or resistance to disease upon hatching, medication can also be administered before hatching. Generally, eggs to be treated are placed on end with the air sac at the top; a small hole is formed through the shell at the top, and an injection needle is passed downwardly through the hole, and desirably into the amnion, into which the medication is discharged. Sometimes the embryo itself is unintentionally injected and may die as a result.

If the medication is a soluble vaccine, unintentional injection of the vaccine into the air sac can be effective, however cell-associated vaccines are typically ineffective if injected into the air sac. Egg injection methods and devices are described in Sharma et al., U.S. Pat. No. 4,458,630, Christensen, U.S. Pat. No. 4,604,968, and Hebrank, U.S. Pat. Nos. 4,681,063 and 4,903,635. As described above, injection of medication into the amnion makes the entire quantity of the medication immediately available to the embryo.

Of particular concern to the poultry industry is the disease known generally as coccidiosis, caused by protozoal parasitic organisms of the genus Eimeria. See, generally, "Coccidiosis", pp. 153-157, in *Avian Disease Manual*, C. E. Whiteman and A. A. Bickford, eds., Kendall/Hunt Publishing Co., 1989, the disclosure of which is incorporated herein by reference. Active and passive immunizations of adult poultry against this disease have been successfully performed on commercial scales for many years. However, only limited success has been achieved in broiler chickens. The reason is that broilers routinely reach market by 6 weeks of age. Using conventional methods of commercial-scale immunization, this is simply not a sufficient time period for the bird's immune system to develop protective immunity.

A procedure termed "trickle vaccination" has been used as a possible route by which effective immunity can be achieved in juvenile poultry. This procedure, as provided in the "Cocci-Vac" product available from Sterwin, Inc., requires that 200 oocysts (a developmental stage in the life-cycle of the Eimeria parasite) be administered per os to each chick within the first 2 days after hatching. When this number of oocysts is ingested during the early neonatal period, the chick typically will immediately develop protective immunity. While from a theoretical viewpoint this method of vaccinating juvenile poultry against coccidiosis may have merit, from a practical standpoint there has not, to date, been a feasible commercial-scale method demonstrated to insure that each chick ingests the required 200 oocysts. See, e.g., P. L. Long et al., Exp. Parasitol. 16:1-7 (1965), N. N. Sharma, J. Parasitol., 50:509-517 (1964), and M. E. Rose et al., Parasitol., 102:317-324 (1990).

SUMMARY OF THE INVENTION

The present invention provides a method for the delivery of medicaments to newly hatched, domestically raised poultry, comprising the steps of:

(a) sequentially and individually orienting the poultry in a manner that facilitates access to the skin covering the residual yolk sac of each individual chick, and (b) injecting an effective amount of the medicament through the skin and into the yolk sac of each oriented chick.

It has been discovered that the residual yolk sac of newly hatched poultry provides a desirable and effective site for the injection of medicaments to poultry. Particularly suprising, is the fact that the yolk sac route allows the administration of medicaments not previously shown to be efficacious by other, traditional, routes of injected administration. For instance, it has been found that the administration of oocysts of the parasite Eimeria tenella, the causative agent of the common disease coccidiosis, successfully protects broiler chicks against a subsequent challenge with oocysts. Such protection has not been previously achievable by the vaccination of broilers on a commercial scale.

In addition, the yolk sac route has been generally found to be as or more effective as traditional routes of administration, for those medicaments typically administered via such routes. As compared to those traditional routes however, the yolk sac route provides the added advantage of allowing the formulation of medicaments in a manner that takes advantage of the gradual absorption of the yolk sac, per se, for example, in order to provide delayed or sustained release of the medicament.

The residual yolk sac of a newly hatched chick is typically a flattened structure, embedded immediately beneath the skin of the abdomen, and in the chicken, may be two or more centimeters (i.e., approximately ¾ inch) in diameter, thereby providing a large target for administration by injection on an assembly line basis in the manner described herein. The medicament can be administered by any suitable means, e.g., by injecting it via an injection needle through the abdominal skin and into the yolk sac.

In a preferred embodiment, the invention provides a device for the administration of the medicament, the device allowing the rapid orientation of individual poultry in a sequential manner, in order to allow the skin covering the residual yolk sac to be penetrated in a consistent and predetermined manner by an injection needle. A preferred device comprises a wall against which the chick's abdomen can be pressed, the wall including a needle for injecting medicament into the abdomen. With the chick oriented and restrained in an upside-down position, with the chick's abdomen at the level of the needle, the injection of the medicament into the yolk sac is thereby facilitated. The preferred target of the abdomen is that area just ventral to the navel, i.e., below the navel and above the opening of the vent.

DETAILED DESCRIPTION OF THE INVENTION

Figure 1:
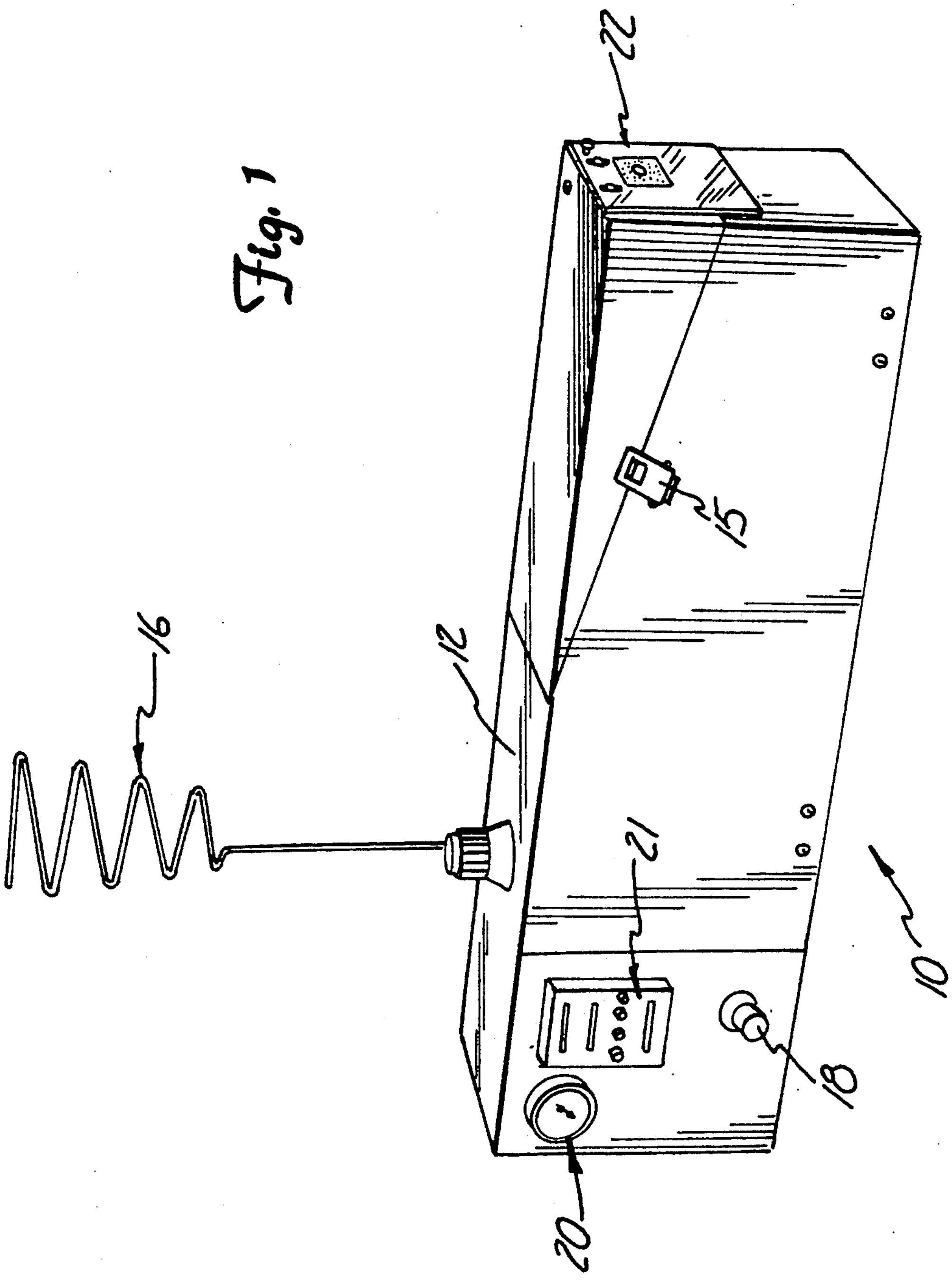
FIG. 1 is a perspective view of a preferred device of the present invention.

The present invention provides a method for the administration of medicaments to various commercially raised poultry (including fowl) species, particularly chickens, turkeys, ducks, geese, guineas, pheasants, and quail. The newly hatched young of domestic poultry will be alternatively referred to herein as "chicks", regardless of species, although it is recognized the young of different species may have different specific names, e.g., turkey hatchlings may be referred to as "poults".

By "medicament" as used herein, reference is made to a wide variety of substances which, when administered to a newly hatched chick according to the method of the present invention, are intended to have a beneficial biological effect upon the chick. Included as medicaments herein are vaccines, nutrients, antibiotics, probiotics, growth stimulators and sexual function modifiers, as represented by the non-limiting list of substances identified below.

The method of the present invention provides a particular advantage in the treatment of coccidiosis in poultry. The common causative agents for this prevalent and devastating disease in turkeys are *E. meleagrimitis*, *E. adenoeides*, and *E. gallopavonis*. The common causative agents in chickens are *E. tenella*, *E. acervulina*, *E. necatrix*, *E. brunetti*, *E. maxima*, *E. mivati*, *E. hagani*, *E. praecox*, and *E. mitis*. The present method provides an effective vaccine for the treatment of coccidiosis. The word "vaccine", as used in this sense, refers to the administration of any material useful for immunizing the chick against coccidiosis. Such material can be either obtained directly, or derived, as by genetic engineering, from the genus Eimeria. Particularly preferred vaccines for such purposes include oocysts and sporozoites of the genus Eimeria.

Prior to the method of the present invention, there did not exist an effective vaccine for this disease, since it appeared that the development of immunity to coccidial organisms could not be achieved simply by conventional injection or by dietary administration of antigenic components.

While not intending to be bound by theory, it would appear that the efficacy of the presently claimed method in vaccinating against coccidiosis may be explained if the yolk sac were to be considered as an extension of the gut in the parafetal and newly hatched chick. The immunobiological tissues, i.e., macrophages, B-cells, and T-cells, are known to interact with gut-associated lymphoid tissues to stimulate cell mediated immunity. In a study of the absorption of colloidal carbon from the yolk of newly hatched chicks, Jeurissen et al., Develop. and Comp. Immunol., 15:437–442 (1991) found that carbon particles were absorbed by the epithelium of Meckel's diverticulum and were transported to leukocytes and mononuclear phagocytes in the underlying lymphoid tissues. Maternal antibodies in the yolk sac may act by "conditioning" coccidial antigens in some way, so as to enhance their immunogenicity.

The presently claimed method and device can also be used to administer vaccines that are, or may become, available for a variety of poultry diseases, including the following diseases:

- Fowl cholera in all fowl species and for which the causative agent is *Pasteurella multocida.*
- Colibacillosis in all poultry and the causative agent for which is *Escherichia coli.*
- Fowl pox, affecting chickens and turkeys and the causative agent for which is fowl pox virus.
- Infectious bronchitis in chickens and the causative agent for which is infectious bronchitis virus.
- Infectious bursal disease (Gumboro) in chickens and the causative agent of which is infectious bursal disease virus.
- Laryngotracheitis in chickens and the causative agent for which is laryngotracheitis virus.
- Leukosis complex, affecting chickens and turkeys, and including the following four major diseases:
  - (1) Marek's disease in chickens, caused by Marek's disease virus,
  - (2) Lymphoid leukosis in chickens, caused by leukosis virus,
  - (3) Reticuloendotheliosis in chickens, caused by leukosis virus,
  - (4) Lymphoproliferative disease in turkeys, caused by leukosis virus.
- Newcastle Disease in chickens and turkeys, caused by Newcastle virus.
- Viral Arthritis in chickens, caused by reovirus.

Antibiotics can be used to prevent or retard early bacterial infections, to promote early growth and to reduce post-hatching stress. Examples of suitable antibiotics include oxytetracycline, chlortetracycline, spectinomycin, cephalosporin, gentamicin, lincomycin, and the quinolones.

Probiotics can be used for the competitive exclusion of such unwanted organisms as Salmonella, pathogenic *E. coli*, *Listeria organisms*, Campylobacter organisms, and for seeding of the gut with desirable organisms. Nutrients include vitamins, minerals, amino acids, sugars, and fatty acids, and can be used for growth promotion and to reduce stress.

Growth promoters are typically endocrine secretions that are used to stimulate growth and feed efficiency. Examples include growth hormone, growth hormone releasing hormone, insulin-like growth factors I and II, avian interleukins (e.g., $aIL_2$), nerve growth factors, thyroxine releasing hormone, thyroxine stimulating hormone, monoiodotyrosine, diiodotyrosine, triiodothyronine, thyroxine and corticosterone.

Sexual function modifiers are typically endocrine secretions that are used to reverse physiological sex, alter time to sexual maturity and/or increase sexual functions in adults. Examples include medullarin inhibitory substance, 17-beta-estradiol, estrone, estrogen, progesterone, testosterone, epiandrostenedione, gonadotropin releasing hormone, follicle stimulating hormone, luteinizing hormone, and prolactin.

Medicaments such as those exemplified above are desirably compounded with physiologically balanced salt solutions to form injectable liquids that can mix with the yolk for absorption into the body with the rest of the yolk. It has been discovered that the normal phospholipid and lipoprotein constituents of the yolk have excellent carrying capacity; they readily adhere to or tolerate medicaments such as those exemplified above.

Medicaments can be administered to the yolk sac of a chick using a hypodermic syringe, and 20 gauge beveled needles are appropriate for this purpose. The use of larger or unbeveled needles appears unnecessary and can tend to have a deleterious effect on the integrity of the yolk sac. Injection volumes of up to about 0.5 ml have been successfully used, this volume being small enough to avoid significant leaking of the injected fluid from the injection site. Injection volumes ranging from about 0.1 ml to about 0.5 ml are preferred.

The yolk sac of a newly hatched chick is substantially flat, and centered on the navel. It generally covers the entire ventral surface of the abdominal cavity. It is generally oval in shape, being about 2.5 cm to 3 cm in its longer (dorsal to ventral) direction, and about 1.5 cm to about 2 cm in width (ventral direction). Within this region, a smaller circular target area is particularly preferred, in that it provides a region of the yolk sac having sufficient depth for, and easy access to, a needle, and at the same time lessens the chance of the needle hitting undesired organs or tissues. The preferred target is a small circular area (having a diameter of about 1 cm, and preferably about 5 mm), with the navel being located approximately half-way between the center of the target area and its 12 o'clock position.

Desirably an automatic vaccinator is used, such as a pneumatic vaccinator (as sold by Vineland Laboratories under the trademark "ViMark") that has been adapted for use in the method of the present invention. The commercial vaccinator has five main parts (see, e.g., "The ViMark Pneumatic Vaccinator Instruction Manual", Vineland Laboratories, Inc., the disclosure of which is incorporated herein by reference):

(1) an aluminum protective body, connected by a hinge to a steel cover plate onto which the chick is placed, (2) a pneumatic cylinder to provide a powerful driving force, together with a shock absorber to eliminate excessive pressure on medicament in the syringe, (3) a pneumatic control unit, including an air filter regulator, air circulation system, external count device, and controls for the adjustment of the needle and activation of the airflow, manometer, and coupling ferrule, (4) a pneumatic retention plate for accurate positioning of each chick, and (5) a syringe assembly, typically including a 0.2 ml syringe capable of providing accurate doses.

The ViMark device employs a push button slide on the top of the device having a central orifice through which a hypodermic needle can protrude. When the button is pushed, as when the neck of a chick is pressed against its surface, the needle quickly extends a given distance beyond the surface of the button and, at the same time, the plunger of the syringe is depressed to inject a given amount, e.g., 0.2 ml of vaccine, into the chick's neck or leg.

Based on the present teaching, those skilled in the art will be able to modify such a device, or design an alternative device, for use with the present invention. In a particularly preferred embodiment, the syringe on the above-described commercial device is re-positioned such that the needle will protrude from the end, rather than top, of the device.

Such a device will be described with reference to the Drawings. FIG. 1 is a perspective view of a preferred device 10 of the present invention, showing aluminum box 12 and steel cover 14, the cover being shown retained in place by a latch 15 and hinges (not shown). The device provides a stiff wire bottle holder 16, a manual activator 18, an air pressure gauge 20, and count meter 21. Of particular note, the device has been provided with a retention plate 22, shown made of plexiglass, stably positioned over the injector end, which serves to both orient and restrain a chick in the desired position.

Figure 2:
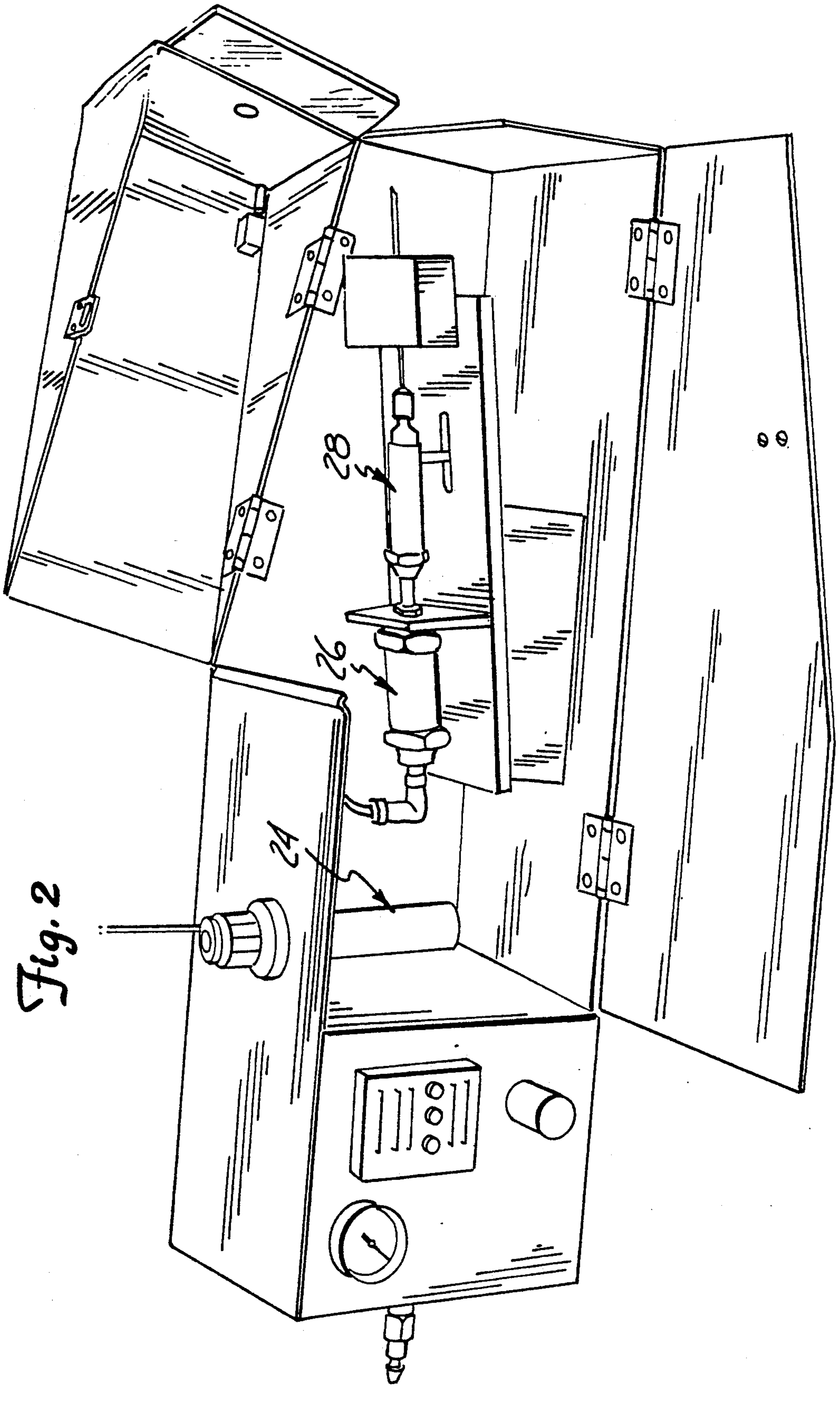
FIG. 2 is a perspective view of the device of FIG. 1, showing the device opened up to reveal inner components.

FIG. 2 is a perspective view of the device of FIG. 1, showing the cover and side of the device opened up to reveal inner components. Clearly seen are the pneumatic control unit 24, the pneumatic drive unit 26, and the syringe assembly 28, which has been repositioned at an angle suitable to allow it to inject through the end of the device, rather than through the top as originally designed.

Figure 3:
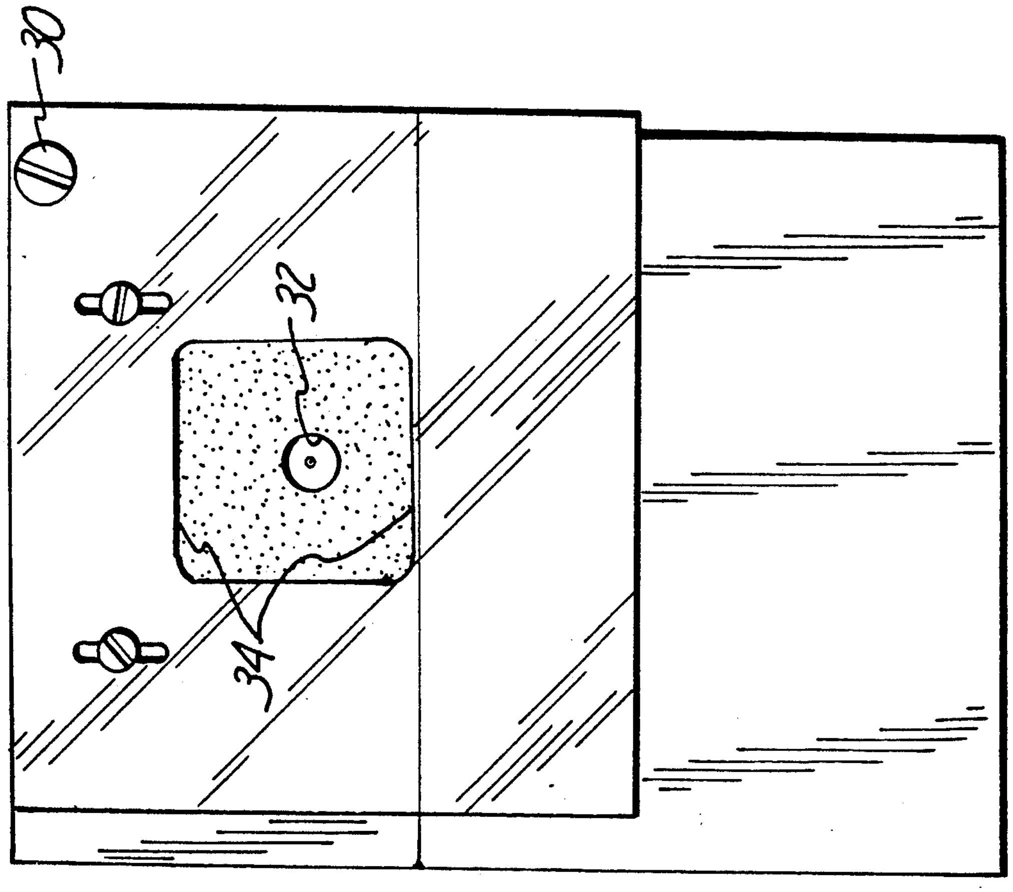
FIG. 3 is a perspective view of the device of FIG. 1 showing the end at which a chick is vaccinated.

FIG. 3 is a perspective view of the device of FIG. 1 showing the end at which a chick is vaccinated, including retention plate 22 and manual firing switch 30. Also seen is the injector hole 32, which has been drilled into the end of steel cover 14 and through which the needle will protrude. Surrounding the injector hole is a larger restraining hole 34, that has been cut in retention plate 22, and which is preferably padded with a soft, cushioning material, such as foam rubber. Hole 34 serves to both cushion the chick and restrain its movement when placed against the injector hole.

Figure 4:
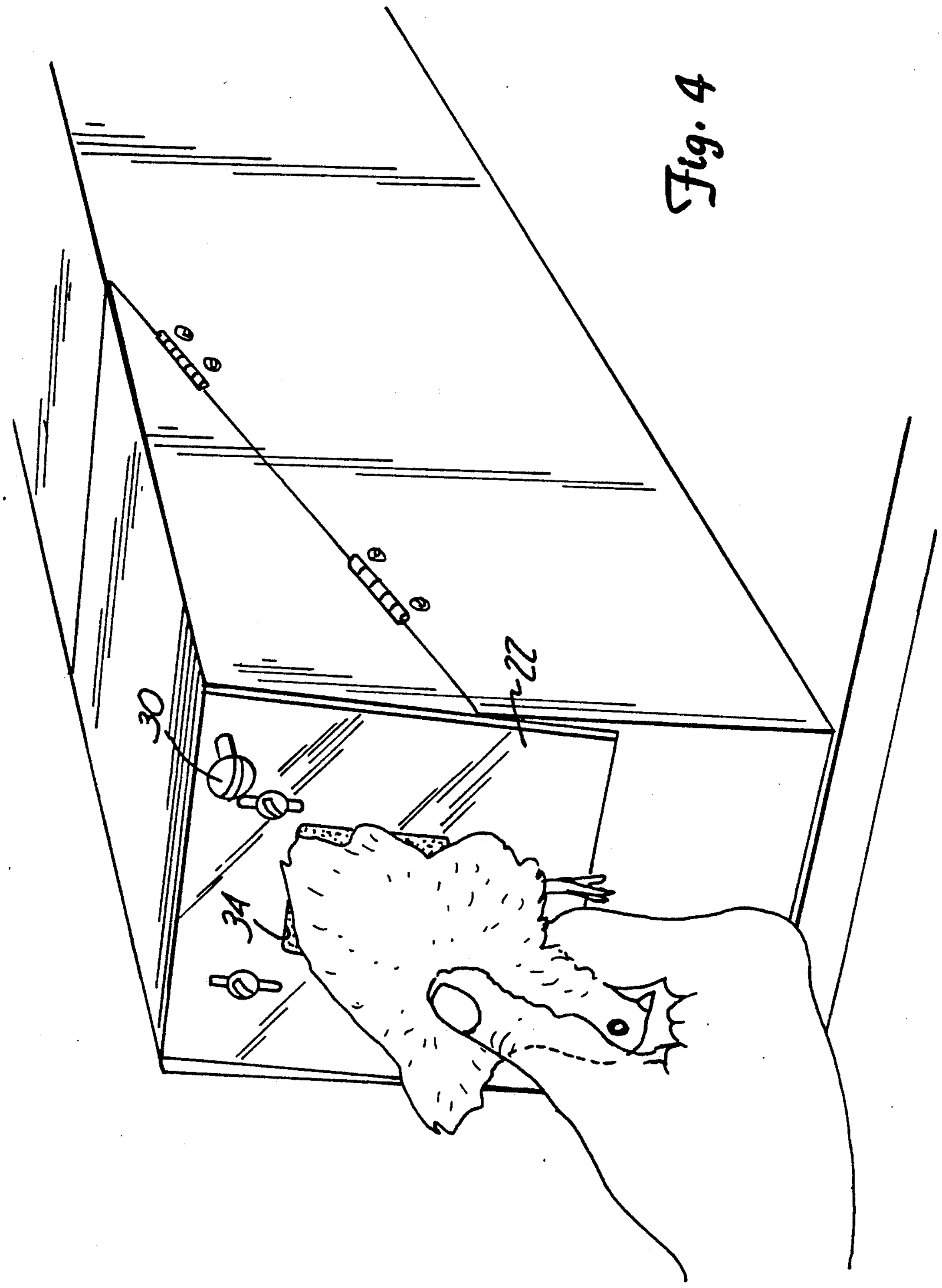
FIG. 4 is a perspective view showing a chick being vaccinated according to the method of the present invention using the device of FIG. 1
Figure 5:
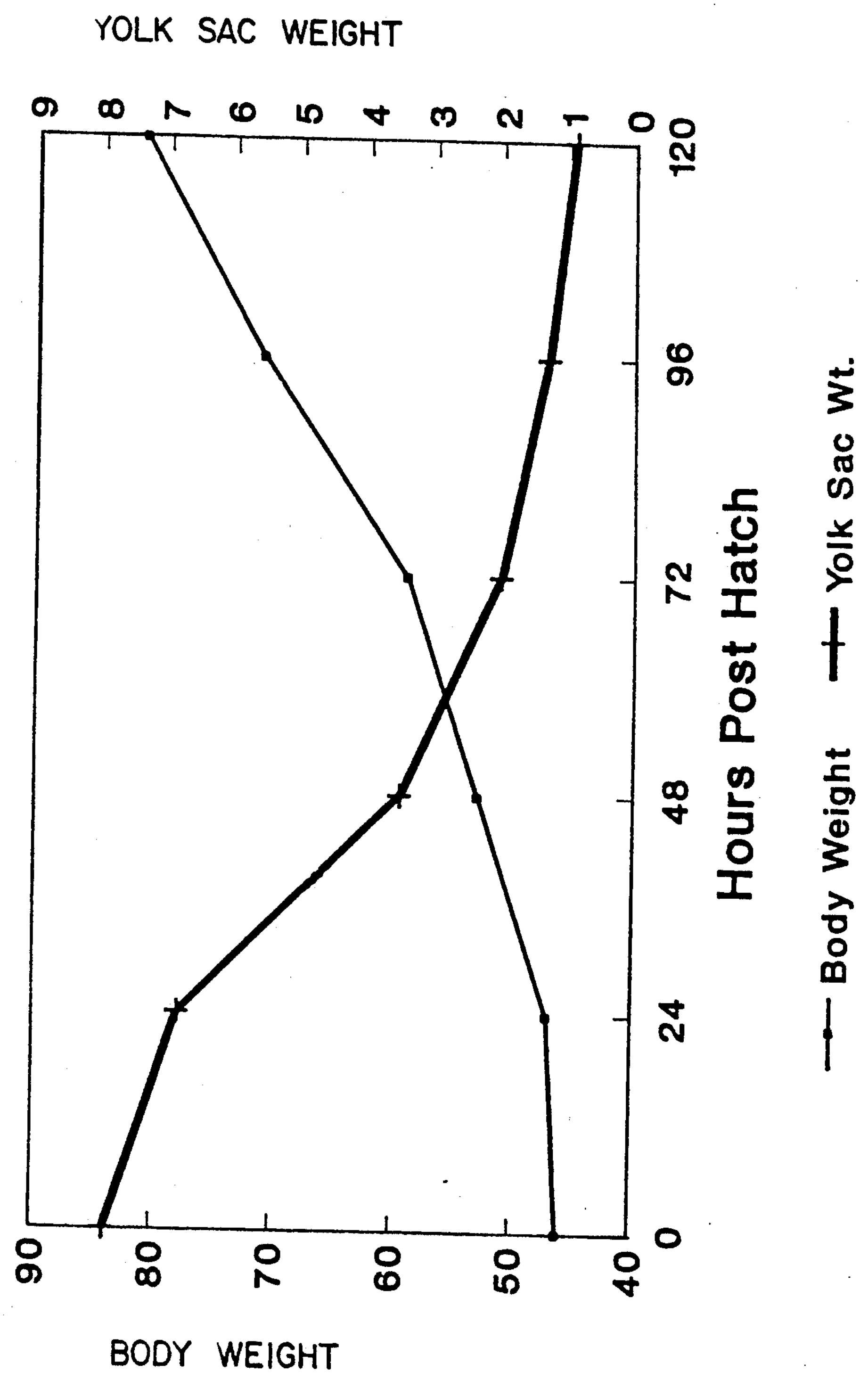
FIG. 5 is a graphic representation of body weights (BW) and yolk sac weights (YSW) of newly hatched broilers over time (post hatch), as described in Example 1, between which parameters the correlation coefficient (r) can be calculated as −0.71.
Figure 6:
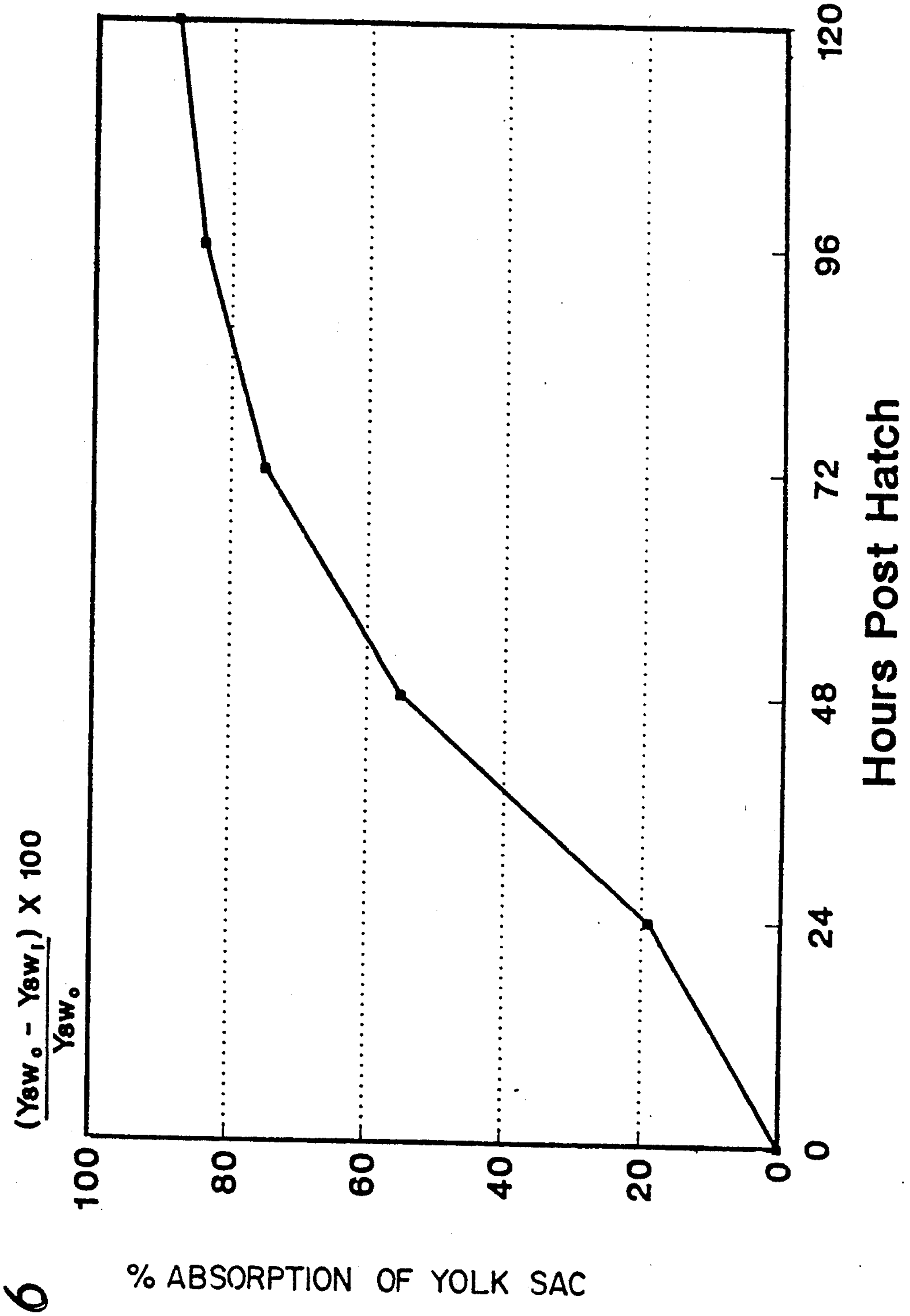
FIG. 6 is a graphic representation of the percentage yolk sac absorption of newly hatched broilers over time (post hatch), as described in Example 1.

FIG. 4 is a perspective view showing a chick being vaccinated according to the method of the present invention using the device of FIG. 1. The chick is held in an upside-down position, with its head between the thumb and fingers of the operator. The desired area of the chick is positioned over the injector hole (not seen) and in an axial relationship with the syringe and needle, and the syringe is activated by depressing firing switch 30. Optionally, and desirably, a pneumatic device can be fitted that allows the syringe to fire automatically at the time the chick is positioned. The needle enters the abdominal area at the desired location and to the desired depth.

In this manner, the chick can be grasped and positioned with its navel facing the needle and the head in the down position. Preferably, the surface against which the chick is pressed upon injection (in this case the plexiglass retention plate) can be modified such that the abdomen of the chick presses against soft material, such as foam rubber, in order to retard movement of the chick during injection and to facilitate accuracy in injecting the yolk sac.

To avoid trauma to a chick, the injection needle should be cleanly and smoothly inserted and removed from the yolk sac. Unwanted damage to the yolk sac and surrounding tissue, with subsequent infection of the damaged area, may result if sideways movement between the needle and the injection site is allowed to occur. Using a pneumatic injector device as described more fully below, the needle is set to protrude a distance of approximately 5 mm from the end of the steel cover. By virtue of the such factors as the bevel of the needle, the thickness of the chick's feathers, any slight air gaps that might exist, and the slight recoil that occurs as the chick is vaccinated, it appears that a needle extending 5 mm beyond the end of the device actually penetrates to a distance of about 1 to 2 mm into the chick'abdomen.

As described more fully in the Examples below, the size of the yolk sac remains approximately constant during the 24 hour period following hatching and then loses weight at a fairly uniform rate. The body weight of a chick similarly changes little during this 24 hour period, but then increases at a fairly uniform rate. Desirably, injection into the yolk sac occurs within approximately the first 24 hours, since after the first 24 hours the yolk sac becomes narrower and smaller, and accordingly is harder to accurately locate.

The invention will be more easily understood by reference to the following non-limiting, illustrative Examples.

EXAMPLES

Example 1

Yolk Sac Anatomy and Physiology

An evaluation was conducted to determine the size, location, and absorption parameters of the yolk sac in newly hatched broiler chicks, from which evaluation preferred parameters were determined for use of the holk sac as a site for the administration of medicaments.

A total of 360 broiler hatching eggs (Arbor Acres X Peterson) were obtained from a commercial broiler hatchery in Mississippi. The eggs were incubated in a commercial-style forced-air incubator. Normal incubating temperatures and humidities were maintained throughout the incubation period. Hatchability was excellent, exceeding 95% hatch of fertile eggs. The hatched chicks were in excellent health and signs of disease were absent.

Twenty-five (25) chicks were selected at random for body weights ("BW") and yolk sac weights ("YSW") at 0, 12, and 24 hr post-hatching. These chicks were held in the incubator until the designated sampling time. Additionally, another 125 chicks were removed from the incubator at 12 hours post-hatching and placed in floor pens in a broiler grow-out house. Twenty-five (25) of these chicks were weighed and sacrificed for YSW's at 24, 48, 72, 96, and 120 hours post-hatching.

During the five-day grow-out (i.e., growth) period, the chicks were fed a conventional corn-soy starter diet containing 1425 kcal/lb (3139 kcal/kg) of metabolizable energy, 20% (by weight) protein and all known nutritional requirements were met or exceeded. Whole-house brooding using liquid propane gas brooders, as well as infrared hotspot brooders, were employed. The chicks were housed at approximately 0.75 $ft^2$ (0.23 $m^2$) per bird density in floor pens. Pine shavings were used as litter. Lighting was provided by incandescent bulbs and the photoperiod was 23 LID (23 hour light period in a day). Such environmental conditions have consistently resulted in superior production performance in this facility.

The BW's and YSW's are expressed below in grams, and relative YSW's ("RYSW") are calculated as g YS/100 g BW. Statistical correlations of BW to YSW over the time course of the experiment were computed using the General Linear Models Procedures of the Statistical Analysis System (*Statistical User's Guide,* 1985, SAS Institute, Inc., Cary, NC).

TABLE 1

| | Hours post-hatch | | | | | | | |
|---|---|---|---|---|---|---|---|---|
| | Incubator | | | Grow-out House | | | | |
| X ± SEM | 0 | 12 | 24 | 24 | 48 | 72 | 96 | 120 |
| BW | 47.04 ± 0.69 | 45.80 ± 0.55 | 46.67 ± 0.75 | 47.87 ± 0.72 | 53.24 ± 0.75 | 59.60 ± 1.01 | 71.28 ± 1.01 | 81.96 ± 1.35 |
| YSW | 7.90 ± 0.25 | 7.30 ± 0.24 | 6.41 ± 0.25 | 6.77 ± 0.32 | 3.56 ± 0.24 | 1.94 ± 0.23 | 1.28 ± 0.22 | 0.95 ± 0.09 |
| RSYW | 16.76 ± 0.43 | 15.88 ± 0.42 | 13.64 ± 0.38 | 14.04 ± 0.52 | 6.61 ± 0.40 | 3.23 ± 0.37 | 1.80 ± 0.24 | 1.18 ± 0.13 |

The tabular results of BW's, YSW's, and RYSW's are presented in Table 1. Graphic presentation of the summarized results are included in FIGS. 1 and 2. Growth, as indicated by BW's at 24 hr posthatching in the birds kept in incubators continuously, as well as in those incubated for 12 hr then placed in the grow-out house for an additional 12 hr, were nearly identical. However, after growth commenced, a near linear increase in BW's was apparent throughout the five-day post-hatching grow-out period.

During the first 24 hr, post-hatching yolk sac absorption, as indicated by YSW's and RYSW's in Table 1 and percentage absorption of yolk sac in FIG. 2 was approximately 20% (by weight). Most absorption of the yolk sac occurred from 24 to 72 hr post-hatching. However, at the end of the 120 hr observation period, approximately 10% of the yolk sac weight was still present. These results indicate that the yolk sac is not completely absorbed until about five days post-hatching.

As shown in FIG. 1, there was an apparent negative relationship between BW and YSW. Specifically, as BW's increased, YSW's decreased. Statistical comparison of these parameters indicated that a significant negative correlation (r) of −0.71 occurred. It is clear that yolk sac absorption starts before growth is initiated; however, after growth starts, there is a rapid and continuous absorption of the yolk sac.

The general appearance of the yolk sacs at necropsies was evaluated. At 0, 12 and 24 hr post-hatching, the yolk sac appeared to fill a large portion of the abdominal cavity. The sac was flat and generally covered the entire ventral surface of the cavity. However, at 48 hr post-hatching, the sac was more elongated. At this time, the most prominent abdominal structure was the gizzard. The yolk sac did not cover the gizzard; rather, the yolk sac was posterior to the gizzard. At this time, the yolk sac had become a more elongated and thicker structure. At later times of necropsy, the yolk sac appeared to become smaller, rounded, and ball-shaped. A final observation, at all times of necropsy, was that the yolk sac was typically streaked with a greenish substance.

These results show clearly that the yolk sac is at maximum size immediately post-hatching and that this size is maintained for at least 24 hr post-hatching. Additionally, the yolk sac appeared flat and covered most of the ventral abdominal surface during the first 24 hr post-hatching. Injection into an area the size of a quarter (2 cm diameter) with the umbilicus half-way between central point and the 12 o'clock position of the circle would ensure penetration of the yolk sac. After 24 hr post-hatching, hitting the yolk sac intra-navel injection would be more difficult because the size and shape of the yolk sac are changing continuously.

The yolk sac would easily accommodate an injection volume of about 1 ml during the 0 to 24 hr post-hatching period. Based upon the kinetics of absorption, if a medicament is formulated so as to be bound up by the yolk sac, the compound could then be metered into the blood stream for at least five days and possibly for as long as 10 days. This estimate is based upon the finding that only 90% yolk sac absorption was completed at 120 hr (5 days) posthatching. If this curve was extrapolated, approximately 10 days would be required for complete yolk sac absorption.

The finding of a greenish material in the yolk suggested a heretofore unrecognized phenomenon. Specifically, bile may enter the yolk sac from the intestine, where it could emulsify fats, resulting in a vital part of the digestive process occurring within the yolk sac. This reinforces the theory described earlier, regarding the yolk sac as a possible extension of the gastrointestinal tract in neonatal poultry.

These results support the contention that the intra-navel, i.e., yolk sac, injection route is a viable alternative for injections into newly hatched poultry. Those skilled in the art will be able to perform analogous studies, in view of the teaching provided herein, in order to determine similar parameters regarding the anatomy and physiology of the yolk sac in other poultry species.

EXAMPLE 2

Yolk Sac Administration of Test Substances

In a preferred embodiment, the presently described intra-yolk sac ("IYS"), method of inoculating substances into the yolk sac of newly hatched chicks can be accomplished by slight adaptation of the methods and devices presently used for conventional subcutaneous injection methods, i.e., injection in the back of the neck (SQ). In this manner, IYS injections can be made in commercial hatcheries with minimal changes in existing personnel, equipment or productivity.

The present Example compares the two methods, using commercially hatched chicks and on-line preparations of Marek's vaccine and antibiotic. Productivity of chicks treated with both methods were compared. Results indicate that the IYS method is indeed commercially feasible.

A total of 3,000 broiler chicks (Arbor Acres X Arbor Acres) were obtained from a commercial hatchery in Carthage, Miss. The chicks were transported to the experiment site in a heated van and treated, approximately 24 hours after hatching.

Three treatments were employed:

1. Non-injected controls ("Non-Inj")
2. Sub-cutaneously injected chicks ("SQ")
3. Intra-yolk sac injected chicks ("IYS")

The Non-Inj chicks were not treated and thus served as controls for the experiment. The SQ chicks received 6,000 plaque forming units (p.f.u.) of CEVA strain of HVT-INOVAC® (Marek's vaccine prepared for use in broiler chickens, Sanofi Animal Health, Inc., Overland Park, KS) plus 0.2 mg of Garasol® (gentamicin, ASL Laboratories, Schering-Plough Animal Health, Inc., Kenilworth, NJ) in 0.20 ml of CEVA diluent for use with injectable vaccines in broilers (Sanofi Animal Health, Inc., Overland Park, KS). Injections were made into the backs of the necks according to common vaccination techniques using the Vineland "ViMark" (model ViMark) automated pneumatic vaccinator. A 20 gauge needle was set to extend a distance of 5 mm and 60 ("p.s.i.") pounds per square inch (52.8 kg per square cm) air pressure activated the injection syringe.

The IYS injected birds were given the same solutions and dosages as the SQ injected chicks. The treatment difference, however, was site of injection. The 20 gauge needle was set to extend a distance of 5 mm for injection into the navel region. This was accomplished by removing the automatic firing switch and chick-positioning blocks. Thus, the chick's abdomen was placed over the needle entry port on the injection platform. When the automatic firing switch injection was activated, the needle entered the abdomen and the vaccine plus antibiotic was deposited directly into the yolk sac. Accuracy of injection, i.e. the percentage of all injections actually entering yolk sac, was determined to be approximately 97%.

After vaccinations were completed, chicks were placed in heated floor pens in a broiler grow-out facility. These pens were supplied with fresh pine shavings as litter. Each pen was equipped with an infrared heat lamp as a brooding source of heat. Additionally, the environmental control system of the house insured ambient temperatures of 85°±3° F. (29.4°±1° C.) for the first two weeks of the experiment. During weeks 3-5, the house temperature averaged 82° F. (27.8° C.) and during week six, the house temperature average 88° F. (31.3° C.).

Chicks were fed standard starter grower rations on an ad libitum basis. Coban®, which is an ionophore anti-coccidial feed additive of broilers, and identified as "Monensin sodium" (Elanco Production Division, Eli Lily, Co., Indianapolis, IN), was added to both rations at 90 g/ton (99 mg/kg); antibiotics and other medicaments were excluded from the rations.

Fifty chicks were started in each floor pen and density was approximately 0.9 $ft^2$ (0.28 $m^2$) per chick. Each pen was supplied with one tube-type feeder and an automatic chick drinking fountain. The lighting regime was constant light for the first 2 weeks and 23 LID thereafter. The one hour of darkness was from midnight until 1:00 a.m. The light source was one, 40 watt incandescent bulb per pen.

Chicks were weighed on Day 43 to determine final body weights. Feed conversion ratios were determined over the entire 43 day grow-out period. These conversions were adjusted for mortalities. Since a majority of the mortalities occurred during the sixth week (due to heat stress) adjustments were made only for mortalities during this time period. All mortalities were necropsied to ascertain cause of death.

Body weights and feed conversion ratios at 43 days of age are presented in Table 2. The data indicate that Non-Inj chicks exhibited significantly heavier final body weights than both treated groups (statistical comparisons were made by a one-way analysis of variance which is a part of the General Linear Models Procedures of the Statistical Analysis System, Statistical User's Guide, 1985; SAS Institute, Inc., Cary, NC). Additionally, the IYS injected chicks had body weights which averaged 2.38% heavier than the SQ injected birds. However, this was not a significant (P≦5%) difference.

Feed conversion ratios were not statistically different (P≦5%) among the three treatment groups. Additionally, the variance in feed conversions among replicate groups composing each treatment was low, suggesting uniform feed conversion.

Mortality rates are presented in Table 3. The mortality rates were calculated as percentage mortality occurring between Days 0 to 36, and Days 37 to 43 and over the entire 43 day grow-out period. Significant differences (P≦5%) in mortality rates were not found during any of the periods. Necropsies of mortalities revealed consistent patterns. During the Day 0 through Day 36 period, the mortalities found in Non-Inj and SQ injected chicks were for various reasons, including accidental deaths, starve-outs, and intestinal strangulations. However, mortalities in the IYS injected group were almost exclusively caused by a trauma-induced infection of the yolk sac. During the Day 37 through 43 period, mortalities in all three groups were generally caused by heat prostration.

The results show clearly that the IYS method of vaccinating chicks can be used in commercial hatcheries. This finding is supported by the fact that IYS vaccinated chicks had heavier body weights than SQ chicks, the latter having been vaccinated by the method presently used in commercial hatcheries on a world-wide basis. Additionally, the finding that Non-Inj chicks were significantly heavier than either of the vaccinated groups is not surprising. The process of vaccination is traumatic to newly hatched chicks and a delay in initiation of growth is not unexpected. It should be noted, however, that none of the birds in this study were exposed to Marek's disease. Had they been exposed, the results would have undoubtedly differed. Specifically, the Non-Inj controls would have been susceptible to Marek's disease with accompanying death and minimal productivity would have been expected.

TABLE 2

Body weights and feed conversion ratios at 43 days of age in chicks vaccinated SQ and IYS methods

| Parameter | Non-Inj. Con.[1] | SQ Inj.[2] | IYS Inj.[3] |
|---|---|---|---|
| BW (lbs) | 4.62* (2.1 kg) | 4.37 (1.98 kg) | 4.47 (2.03 kg) |

TABLE 2-continued

Body weights and feed conversion ratios at 43 days of age in chicks vaccinated SQ and IYS methods

| Parameter | Non-Inj. Con.[1] | SQ Inj.[2] | IYS Inj.[3] |
|---|---|---|---|
| F.C.[4] | 1.85 | 1.88 | 1.86 |

[1]Non-Inj. Con. = not vaccinated
[2]SQ Inj. = 1-Day old chicks vaccinated in the neck with 6,000 p.f.u. of HVT and 0.2 mg Garasol in a diluent volume of 0.2 ml.
[3]IYS Inj. = 1-Day old chicks vaccinated in the yolk sac with 6,000 p.f.u. of HVT and 0.2 mg Garasol in a diluent volume of 0.25 ml.
[4]F.C. = Feed conversions which are corrected for mortalities during Days 37-43.
*A mean in a row with this symbol differs significantly from the other two means at a probability level of 5%.

TABLE 3

Mortality rates (%) of 43 day old broilers vaccinated by SQ and IYS methods

| Period (days) | Non-Inj. Con[1] | SQ Inj.[2] | IYS Inj.[3] |
|---|---|---|---|
| 0–36 | 2.8 | 3.8 | 3.8 |
| 37–43 | 9.4 | 4.8 | 9.0 |
| 0–43 | 12.2 | 8.6 | 12.8 |

[1]Non-Inj. Con. = not vaccinated
[2]SQ Inj. = 1-Day old chicks vaccinated in the neck with 6,000 p.f.u. of HVT and 0.2 mg Garasol in a diluent volume of 0.2 ml.
[3]IYS Inj. = 1-Day old chicks vaccinated in the yolk sac with 6,000 p.f.u. of HVT and 0.2 mg Garasol in a diluent volume of 0.25 ml.

Since feed conversions varied little among the groups, it can be concluded that the treatments did not alter basic metabolism. Growth and development, as indicated by feed conversions, were also normal in all groups.

The mortality rates during the first 5 weeks suggest that the IYS method did not cause an increased level of mortality, as compared to the SQ method. However, the finding at necropsy that injection associated trauma occasionally occurred in the yolk sac region demonstrates that the IYS method needs to be performed with particular care.

In order to lessen the chance of trauma, the above-described method of injecting the chicks IYS using a conventional chick vaccinator can be improved, for instance, by the use of a cushion prepared from a soft, pliable substance, such as foam-rubber. The cushion can be applied in such a manner that when the chicks are positioned over the needle entry port, the cushion will prevent the chicks from moving as the injection is made. It has been observed that trauma was minimized when the chick did not move during needle entry. The firing switch can be mounted on the positioning bar, so that injection is triggered by placing the chicks against the positioning bar.

During week six of this study, the experimental facility, in Mississippi, experienced the hottest week of the summer. Industry reports of 10–15% mortality rates in finishing broilers were commonplace. Eleven fans were placed in the grow-out facility in an attempt to maximize ventilation of the house. Nevertheless, the 100° to 105° F. (37.8° to 40.6° C.) temperatures with relative humidity of 50–75%, resulted in an average mortality rate of 11.2% during this period of extreme heat. Significant differences (P≦5%) in mortality rates among the treatment groups, however, were not found.

As can be seen by these results, the IYS method for introducing medicaments into newly hatched chicks appears to be adaptable to commerical practices. Existing hatchery personnel will be able to master this technique without extensive re-training and re-orientation.

Productivity, i.e. number of chicks injected per hour (2,500–4,000/hour), should not be affected by this method, since the same or similar movements are involved as with the SQ method.

EXAMPLE 3

Comparison of Administration Routes

An experiment was performed to determine the optimal injection depth and volume, as well as the extent of any injury to the yolk sac.

Chicks: One hundred sixty (160) newly hatched male chicks were acquired from Choctaw Maid Hatchery in Carthage, MS. Fifty (50) chicks were assigned to each of three treatment groups. Needles (20, 22, or 25 gauge) were fitted with a cork to regulate injection depth to 1, 3, or 5 mm. Injections were made using the needles attached to disposable plastic syringes into the umbilical (navel) region to determine the desired injection depth which would penetrate the yolk sac. following this determination, injection of a solution of methylene blue in saline was made. Volume selection was made by determining the volume that would be accepted into the sac with minimal leakage. Chicks were sacrificed, then necropsied post-injection to determine if damage and/or leakage occurs.

Treatment 1: Sham controls.
- Treatment 1a: Dirty Needle Sham Controls. Twenty-five (25) chicks received a sham injection (needle insertion followed by immediate removal). The needle was not changed between chicks; thus, the potential for needle-induced contamination would be expected to occur.
- Treatment 1b: Clean Needle Sham Controls. Twenty-five (25) chicks received sham injections and each injection was made with a sterile needle.

Treatment 2: Saline Injections.
- Treatment 2a: Dirty Needle Saline Injections. Twenty-five (25) chicks received a dose of 0.85% saline (depth and volume as per Treatment 1). Needles were not changed between injections.
- Treatment 2b: Clean Needle Saline Injections. Twenty-five (25) chicks received a dose of saline and a sterile needle was used for each injection.

Treatment 3: Glucose Injections.
- Treatment 3a: Dirty Needle Glucose Injections. Twenty-five (25) chicks were injected with a 5% glucose solution (depth and volume as per Treatment 1). The needle was not changed between injections.
- Treatment 3b: Clean Needle Glucose Injections. Twenty-five (25) chicks received a dose of 57% glucose solution using a sterile needle for each injection.

Parameters of Measurement: Only male chicks were used. Body weights were determined on each chick (banded for individual identification at hatch) at the time of assignment to treatments and at 13 and 35 days of age. Ten (10) chicks were sacrificed and YSW's determined to establish a baseline for newly hatched chicks. Then three (3) chicks from each of Treatments 1a, 1b, 2a, 2b, 3a, 3b were sacrificed for YSW's at three days post-treatment; i.e., non-absorbed yolk sacs were weighed. Mortalities were recorded daily and each dead chick was necropsied in an attempt to determine the cause of death.

Chicks were fed a standard experimental broiler starter ration (see Example 1) for the first 10 days and a standard experimental broiler grower ration was then fed until termination of the experiment. These rations met or exceeded all known nutritional requirements of the chicks as described by the National Research Council, U.S. Academy of Science, 1985, Washington, DC.

The bird density was 0.9 $ft^2$ (0.28 $m^2$) per chick for this experiment, and fifty (50) chicks were placed in each of 3 pens.

The chicks received the diets described above, as well as water on an ad libitum basis. The starter ration was placed in cardboard lids directly on the litter for the first three days. This procedure allowed the newly hatched chicks intimate contact with the feed and the process of establishing uniform feeding behavior by all of the chicks was maximized. Thereafter, rations were available to the chicks in hanging tube feeders. Water was provided in automatic drinking fountains (Plasson® fountains, Diversified Imports, D.I.V. Co., Lakewood, NJ). One feeder and one water fountain was available in each pen.

The lighting regime consisted of constant light for the first 14 days. Thereafter, the lighting consisted of 23 LID, with the one hour of darkness being from midnight until 1:00 am. The light source was one, 40 watt incandescent bulb for each pen.

Each pen was equipped with an infrared heat lamp as a brooding source of heat. The heat lamps were used as needed during the first 14 days to insure maximum chick comfort.

The house was a steel prefabricated building, situated on a concrete slab. The side walls were conventional pulley-operated curtains and the end walls and ceiling were fully insulated (R-value=+25). Each pen was supplied with fresh pine shavings as litter. Exhaust fans, as well as intake fans, for fresh air were located at opposite ends of the building. The intake air was forced through a plenum to condition the air, (auxiliary heater or dehumidifier) before it entered the general circulation.

The environmental controls systems of the house insured temperature of 85°±3° F. (29°±1° C.) for the first 14 days regardless of season of the year and 75°±3° F. (24°±1° C.) for the remainder of the 6-week grow-out period, regardless of the season. Regulation of house temperature was always made on the basis of maximum chick comfort.

The paired intake and outlet fans (at opposing ends of the house) were regulated to operate 15 sec/10 min for the first seven days and for 45 sec/10 min for days 8 through 14; thereafter, ventilating was regarded as a part of the total bird comfort factor.

The following schedule was maintained:

| Day | Event |
|---|---|
| 0 | Hatch 160 chicks, transported to experimental facility. |
| 0 | Sacrifice 10 chicks and determine YSW's. |
| 0 | Band remaining chicks, body weights, make injections, allot chicks to proper pens. |
| 3 | Chick sacrifice-3 chicks from treatments 1a, 1b, 2a, 2b, 3a and 3b sacrificed and necropsied, BW's and YSW's determined. |
| 12 | BW's of all chicks taken and feed ration change to grower feed. |
| 45 | Final BW's taken. |
| 0–45 | Birds checked daily to ensure proper management. |

Results are summarized in Tables 4–6. Body weights of treatments are presented for 2-and 5-week old birds in Table 4. An asterisk indicates that the mean weight was statistically different from the other treatment groups of the same age. The upper mean is expressed in grams, while the corresponding mean in parenthesis is expressed in pounds. YSW's are not presented because no statistical differences were found between the groups. A comparison of all birds treated with non-sterile versus sterile needles, regardless of individual treatment categories, is provided in TABLE 6. The livability of the birds (the number still alive at 2 and 5 weeks, expressed as a percentage of those at day 0), is provided in TABLE 7.

Statistical comparisons were made using a one-way analysis of variance as described above.

TABLE 4

| Treatments | Age (wks) 2 | 5 |
|---|---|---|
| | Grams (lbs) | |
| Control | 203.1* | 1426 |
| | (0.45) | (3.14) |
| Saline, 0.5 ml | 212.1* | 1430 |
| | (0.47) | (3.15) |
| Glucose, 0.5 ml | 196.5* | 1395 |
| | (0.43) | (3.07) |

TABLE 5

| Needle Condition | Age (wks) 2 | 5 |
|---|---|---|
| | Grams (lbs) | |
| Sterile | 203.0 | 1375 |
| | (0.45) | (3.08) |
| Non-sterile | 206.0 | 1434 |
| | (0.45) | (3.16) |

TABLE 6

| Treatment | Age (wks) 2 | 5 |
|---|---|---|
| | Grams (lbs) | |
| Control | 93.2 | 93.2 |
| Saline, 0.5 ml | 90.1 | 90.1 |
| Glucose, 0.5 ml of 5% solution | 93.3 | 92.3 |

It can be seen that at two weeks of age, the chicks that were injected with saline were significantly ($P \leqq 5\%$) heavier than those injected with glucose. The weights of the control birds were intermediate to saline and glucose injected birds. At five weeks, however, significant ($P \leqq 5\%$) differences among BW's of the three treatments were not found.

Body weights of birds, based on whether a sterile or dirty needle was used, are presented in Table 5. The use of a sterile needle did not appear to alter growth of the chicks.

Liveability results are presented in Table 6. Normal liveability was noted in all groups.

A preferred procedure for manual injection by the IYS route was determined to be as follows: Grasp the chick in one hand, holding such that the umbilical (navel) region is visible; with the other hand insert a 1-inch (2.5 cm) long, 20 or 22 gauge needle into the abdominal area, with the target being a circle around the umbilicus not to exceed 1 cm in diameter. The umbilicus should be between the center and 12 o'clock position of the circle. The preferred depth is 3 mm. This can be accomplished by placing a cork stopper over the needle such that only the final 3 mm of the needle is exposed. A quick jab is required to puncture the skin and underlying tissues over the yolk sac. The desired volume is 0.5 ml of solution. This volume when injected will result in minimal leakage from the sac. The needle should be removed and then the next chick should be injected. The total time for one hand injection is 2-3 seconds.

The results of this experiment indicate clearly that the IYS administration of "Generally Regarded as Safe" (GRAS) compounds, i.e. saline and glucose, were not harmful to day-old broilers. The increased BW in the saline-injected chicks at two weeks was probably due to a positive hydration effect. Additionally, the negative growth effect caused by the injection of glucose was probably due to a near toxic dose of glucose.

The results at five weeks, i.e., normal growth and livability regardless of treatment and sterility of the needle, indicated that the IYS method is safe for broilers reared under floorpen conditions.

Example 4

Vaccination Against Coccidiosis Under Laboratory Conditions

A total of 675 newly hatched broiler chicks were obtained from a hatchery in Philadelphia, MS. These chicks were individually wing-banded to facilitate chick identification. Chicks were assigned in groups of 15 chicks to 45 pens. The pens were located in heated, metal battery cages. The cages were maintained in an environmentally controlled room which insured constant temperatures between 80° and 85° F. (27° and 29° C.). The battery cages were equipped with thermostatically controlled heaters and brooding temperature was maintained at 90° F. (32° C.) for days 0-7, 85° F. (29° C.) for days 8-14, and 75° F. (24° C.) thereafter. The room was lighted by overhead florescent fixtures and continuous lighting was provided.

The chicks in treatments 1-8 below were fed ad libitum a standard corn soy diet containing no added fat. This ratio met or exceeded all known nutritional requirements of the chicks as described by the National Research Council, U.S. Academy of Science, Washington, D.C. (1985). The diet of treatment 9 was identical to that of the other treatments, with the single exception that BioCox® (an inonophor chemical anti-coccidial with salinomycin sodium as the active ingredient; Agri-Bio Corp., subsidiary of A. H. Robbins Co., Gainesville, GA) was added at 60 grams/ton (66 mg/kg).

Each of the nine treatments were conducted on 5 pens of chicks:

| Treatment | Designation | Vaccination | Challenge |
|---|---|---|---|
| 1 | Neg. Con. | 0 oocysts | None |
| 2 | Pos. Con. | 0 oocysts | Yes |
| 3 | IYS-125 | 125 oocysts IYS | Yes |
| 4 | IYS-250 | 250 oocysts IYS | Yes |
| 5 | IYS-500 | 500 oocysts IYS | Yes |
| 6 | IYS-1000 | 1000 oocysts IYS | Yes |
| 7 | Trickle | 200 oocysts orally | Yes |
| 8 | CocciVac | CocciVac orally | Yes |
| 9 | BioCox | BioCox orally | Yes |

The oocysts for treatments 3-7, as well as oocysts for all challenges were prepared according to accepted experimental procedures. Chickens not used in this study were reared in isolation cages, orally infected with oocysts of *Eimeria tenella*, and sacrificed 5 days after infection. Their intestines were removed, washed to collect the intestinal contents containing the oocysts, and oocysts were harvested. The oocysts then could serve as vaccines or as infective challenges.

Vaccinations for treatments 3–6 were given into the yolk sac using the Vineland ViMark automatic injector, modified as described herein. These injections were given on day 0. Treatment 7, i.e., trickle vaccination, was accomplished by orally gavaging day 0 chicks with 200 oocysts in 1 ml of distilled water. A gavage needle fitted to a 6 cc syringe was inserted into the esophagus, near the crop and the gavage solution was deposited directly into the crop. Treatment 8, i.e., CocciVac ® (a vaccine containing oocysts against 4 species of Eimeria which is recommended to be sprayed on the initial feedstuff of chicks, Sterwin Laboratories, Inc., subsidiary of Pitman Moore, Co., Millsboro, Del.) was orally gavaged into day 0 chicks at a level of 0.1 ml CocciVac in 0.9 ml of distilled water. Treatment 9 did not involve vaccinations, rather the BioCox was added to all feed presented to the chicks at the level previously described.

All chicks were challenged by oral gavage of 50,000 sporulated oocysts (passed through a chicken and recovered to insure infectibility) in 1.0 ml of distilled water on day 21. Since 5 pens of chicks received each of the treatments, each treatment then had 5 replications.

The following schedule was maintained:

| Day | Event |
|---|---|
| 0 | Hatch 675 chicks, transport to experimental facility. |
| 0 | Band chicks, body weights, make injections and gavages, and allot chicks to proper pens. |
| 21 | Weigh all chicks, and challenge with 50,000 oocysts. |
| 28 | Weigh all chicks, then sacrifice and necropsy to determine lesion scores. |
| 0–28 | Birds checked daily to ensure proper management. |

The following measurements were made:

(a) Body weights were taken at time of hatch, at time of challenge, and again 8 days post-challenge. Weight gain was computed for each period.

(b) Lesion scores were assigned separately to left and right cecal pouches 8 days post-challenge. The average lesion score of each chick was then computed. Lesion scores were determined by inspecting each cecal pouch and then assigning a score based on a scale of 0 to 4, with 0 being normal, 1=slight redness and swelling; 2=overt blood in cecal contents, 3=cecal contents congealed, swollen and filled with cellular debris and blood, and; 4=core formation in cecal lumen with extensive tissue damage and sloughing.

(c) Mortalities were recorded on a daily basis and pre- and post-challenge mortalities were calculated.

Statistical comparisons were made using a one-way analysis of variance as described above.

Results of this experiment are presented in TABLE 7. Pre-challenge, i.e. 0–3 week, body weights and mortality rates were not significantly different (P≦5%) among any of the treatments. These results suggest that none of the treatments adversely affected the chicks. Gain as related to the treatments during the weeks immediately following challenge, i.e., 3 to 4 weeks, indicates that all treatments, including the negative controls, reduced gain significantly (P≦5%). However, gain in positive controls was not significantly (P≦5%) different from any of the other treatments. Additionally mortality rates during the challenge period, i.e., 3 to 4 weeks, were not significantly (P≦5%) different among any of the treatment groups. These results indicate that all treatments protected the chicks such that normal growth and livability was ensured.

Cecal pouch lesion scores indicated that only Treatment 9, i.e., BioCox, protected the gut in a manner equivalent to the non-challenged negative controls. However, all IYS treatments were numerically, but not significantly (P≦5%) superior in protecting the gut than the commercially available CocciVac coccidiosis vaccine.

It has been postulated that the lining of the gut must be invaded for the process of immunity to develop when a coccidial vaccine is administered. Ionophore anti-coccidials, however, prevent the Eimeria from entering the lining of the gut, therefore, the absence of cecal lesions was expected. Ionophore anti-coccidials can begin to fail under intense worldwide usage, as parasite populations become resistant to the drug. This drug resistance apparently can occur due to genetic adaptability of the parasite in response to prolonged exposure to the drug.

TABLE 7

Response of chicks vaccinated IYS with sporulated oocysts

| Treatment | Gain (g)[1] (0–3 wk) | Mort. (%)[2] (0–3 wk) | Gain (g)[3] (3–4 wk) | Mort. (%)[4] (3–4 wk) | Lesion Score |
|---|---|---|---|---|---|
| 1 (Neg. Con) | 569[a] | 2.7[a] | 416[a] | 0.0[a] | 0.1[b] |
| 2 (Pos. Con) | 553[a] | 0.0[a] | 379[b] | 2.0[a] | 3.4[a] |
| 3 (IYS-125) | 555[a] | 2.7[a] | 408[a] | 0.0[a] | 3.1[a] |
| 4 (IYS-250) | 555[a] | 4.0[a] | 420[a] | 4.0[a] | 2.7[a] |
| 5 (IYS-500) | 576[a] | 4.0[a] | 401[a] | 6.0[a] | 3.1[a] |
| 6 (IYS-1000) | 569[a] | 4.0[a] | 409[a] | 2.0[a] | 2.8[a] |
| 7 (Trickle) | 541[a] | 0.0[a] | 410[a] | 2.0[a] | 2.8[a] |
| 8 (CocciVac) | 541[a] | 0.0[a] | 391[a] | 2.0[a] | 3.5[a] |
| 9 (Bio-Cox) | 578[a] | 0.0[a] | 430[a] | 2.0[a] | 0.3[b] |

[a–b]Means in a column which possess different superscripts differ significantly at probability of 5%.
[1]0–3 wk Gain is gain from hatching until just prior to challenge with sporulated oocysts.
[2]0–3 wk Mort. is cumulative mortality from hatching until just prior to challenge with sporulated oocysts.
[3]3–4 wk Gain is gain during the week immediately following challenge with sporulated oocysts.
[4]3–4 wk Mort. is cumulative mortality during the week immediately following challenge with sporulated oocysts.

Example 5

Vaccination Against Coccidiosis Under Field Conditions With An Oocysts-Type Vaccine A total of 400 broiler chicks were obtained from a hatchery in Philadelphia, Miss. Chicks were transported to the experiment site in a heated van and treatments were conducted within 24 hours post-hatching.

Chicks were maintained in the broiler grow-out facility described in Example 3. This facility provides conditions that are similar to most commerical broiler grow-out facilities in the United States. The management procedures employed in this experiment were as previously described.

Chicks were wing banded and then assigned to 8 groups of 50 chicks. Each group was maintained in a pen within the grow-out facility. Two groups were assigned to each of 4 treatments. The treatments were as follows:

| Treatment | Designation | Vaccination | Challenge |
|---|---|---|---|
| 1 | Neg. Con. | 0 oocysts | None |
| 2 | Pos. Con. | 0 oocysts | Yes |
| 3 | IYS | 200 oocysts | Yes |

-continued

| Treatment | Designation | Vaccination | Challenge |
|---|---|---|---|
| 4 | per os (oral) | 200 oocysts | Yes |

Treatments 3 and 4 were administered using a suitably modified Vineland ViMark automated, pneumatic chick vaccinator.

In treatment 3, each day 0 chick was injected IYS with 200 sporulated oocysts (prepared as in Example 4). In Treatment 4, each chick was orally gavaged (as per Example 4) with 200 sporulated oocysts.

The following schedule was maintained:

| Day | Event |
|---|---|
| 0 | Hatch 400 chicks, transport to experimental facility. |
| 0 | Band chicks, body and feed weights, make injections and gavages, and allot chicks to proper pens. |
| 7 | Sacrifice 5 chicks from each treatment to assess yolk sac absorption. |
| 21 | Weigh all chicks and feed, then challenge with 50,000 oocysts/chick. |
| 28 | Weigh all chicks and feed, then sacrifice 10 from each pen, necropsy to determine lesion scores. |
| 36 | Weigh all chicks and feed. |
| 0-36 | Birds checked daily to ensure proper management. |

The following measurements were made:

(a) Body weight was taken at time of hatch, at time of challenge, 8 days post-challenge and at 36 days of age. Weight gain during the pre-challenge period (0–3 weeks), challenge period (3–4 weeks) and final grow-out period (4–6 weeks) were computed.

(b) Lesion scores on separate cecal pouches were made (as previously described in Example 4) 8 days post-challenge (3–4 weeks).

(c) Feed Conversion ratios were computed during each period and the ratio was: feed consumed during the period divided by body weight gain during the period.

(d) Mortalities were recorded on a daily basis and computed for each period.

Statistical comparisons were made using a one-way analysis of variance. Results of this experiment are presented in Table 8. During the pre-challenge period (0–3 weeks) significant ($P \leqq 5\%$) differences in body weight gains, mortality rates and feed conversions did not occur. These results indicate that the treatments did not affect normal growth and livability of the early chicks.

However, during the challenge period significant ($P \leqq 5\%$) differences among gains and lesion scores were recorded. Gain in the positive controls was significantly lower than the other three treatments, and the IYS chicks exhibited a significantly lower gain than both the negative controls and trickle-treated chicks. Lesion scores were significantly ($P \leqq 5\%$) lower in the negative controls than all other groups and the trickle-treated chicks had a significantly ($P \leqq 5\%$) lower mean lesion score than the positive controls and the IYS treated chicks.

A single significant ($P \leqq 5\%$) effect was noted during the final grow-out period (4–6 weeks). The negative controls exhibited a lower gain than the positive controls.

These results indicate that, as compared to the controls, both the IYS and trickle treatments provided useful protection to the chicks. The trickle treatment provided somewhat better protection than the IYS treatment, which would be expected, since the administration of 200 oocysts at the preferred time, i.e. early during the post-natal period, is known to provide a high degree of immunity.

TABLE 8

Results of IYS oocyst vaccination of chicks under field conditions

| Parameter | Neg. Con | Treatment Pos. Con | IYS | Trickle |
|---|---|---|---|---|
| Gain (g) (0-3 wks)[1] | 556[a] | 535[a] | 532[a] | 539[a] |
| Gain (g) (3-4 wks)[2] | 395[a] | 343[c] | 365[b] | 393[a] |
| Gain (g) (4-6 wks)[3] | 856[b] | 922[a] | 872[ab] | 880[ab] |
| Mort (%) (0-3 wks)[4] | 2.0[a] | 2.0[a] | 2.0[a] | 2.0[a] |
| Mort (%) (3-4 wks)[5] | 0.0[a] | 2.0[a] | 0.0[a] | 0.0[a] |
| Mort (%) (4-6 wks)[6] | 0.0[a] | 0.0[a] | 0.0[a] | 0.0[a] |
| FC (0-3 wks)[7] | 1.66[a] | 1.66[a] | 1.64[a] | 1.66[a] |
| FC (3-4 wks)[8] | 1.86[a] | 2.06[a] | 1.96[a] | 1.87[a] |
| FC (4-6 wks)[9] | 2.40[a] | 2.25[a] | 2.37[a] | 2.36[a] |
| Lesion Scores (3-4 wks) | 0.49[c] | 3.04[a] | 3.30[a] | 1.47[b] |

[a-c]Means in a row, i.e., for each parameter, which possess different superscripts differ significantly at Probability of 5%.

[1-3]Gain at 0–3 wks is gain before challenge; Gain at 3–4 wks is gain during the week immediately following challenge; and Gain 4–6 wks is gain during the last two weeks of the experiment.

[4-6]Mort at 0–3 wks is cumulative mortality before challenge; Mort at 3–4 wks is cumulative mortality during the week immediately following challenge; and Mort at 4–6 weeks is cumulative mortality during the last two weeks of the experiment.

FC Means feed conversion ratio, i.e. grams of feed consumed per gram body weight gain. FC at 0–3 is feed conversion before challenge, FC at 3–4 wks is feed conversion during the week immediately following challenge and FC at 4–6 wks is feed conversion during the last two weeks of the experiment.

EXAMPLE 6

Vaccination Against Coccidiosis Under Field Conditions with a Sporozoite Vaccine Sporozoites were evaluated as a candidate, in a preferred method of the present invention, for the active component of a coccidiosis vaccine. Sporozoites are the infective stage of the parasite. That is to say, when oocysts are injected, the acidic conditions together with digestive enzymes of the gut excise the oocysts and sporozoites are released. This life form of Eimeria is capable of infecting the target epithelial cells of the gut. Sporozoites may be able to attach to and then enter T-lymphocytes that are intimate with the epithelial lining of the gut. The T-cells would then able to initiate cellular immunity.

A total of 1,000 broiler chicks were used in this experiment. These chicks were obtained from a hatchery in Philadelphia, MS. The management procedures employed in this experiment have been described above (Example 3).

Fifty chicks were assigned to 20 pens in a grow-out facility. Five pens were allotted at random to 4 treatments. Thus, each treatment consisted of 5 replications.

The four treatments were as follows:

| Treatment | Designation | Vaccination | Challenge |
|---|---|---|---|
| 1 | Neg. Control | Oocysts or sporozoites | No |
| 2 | Pos. Control | Oocysts or sporozoites | Yes |
| 3 | IYS | Sporozoites from 200 oocysts | Yes |
| 4 | Trickle | 200 oocysts orally | Yes |

Treatment 3, i.e., the IYS-treated chicks, received 200 sporozoites which were collected by excisting 200 sporozoites. The excisting procedure was performed as outlined by Hofmann and Raether (Parasitol. 76:479–486 [1990)). A known number of oocysts were placed in a centrifuge tube and spun to form a pellet.

The supernatant was decanted and replaced with Hanks balanced salt solution (HBSS). Glass beads, 1 mm in diameter, were placed in the oocyst suspension and spun in a vortex until all oocysts were ruptured. The released sporozoites were washed free of the glass beads, then spun in a centrifuge tube to form a pellet. The sporozoites were then placed into 100 ml HBSS containing 0.25% trypsin and 4% taurodeoxycholic acid. The suspension was incubated in a shaking water bath for 90 min at 41° C. The sporozoites were then spun to form a pellet, resuspended in HBSS and used as the vaccine. Treatment 4, i.e., trickle-treated chicks, received 200 sporulated oocysts by oral gavage as described previously (Example 4).

Treatments 2, 3, and 4 were challenged on Day 21 by oral gavage with 50,000 oocysts/chick.

The following measurements were made:

(a) Body weights were taken at time of hatch, at time of challenge and 8 days post-challenge.

(b) Lesion scores (as in Example 4) were taken 8 days post-challenge in one pen of chicks from each treatment.

(c) Mortalities were recorded on a daily basis and pre- and post-challenge mortality rates were computed.

(d) Feed conversion ratios were computed (see Example 5) pre- and post-challenge.

The following schedule was maintained:

| Day | Event |
|---|---|
| 0 | Hatch 1,000 chicks, transport to experimental facility. |
| 0 | Band chicks, body and feed weight, make injections and gavages, and allot chicks to proper pens. |
| 21 | Weigh all chicks and feed, then challenge with 50,000 oocysts/chick. |
| 28 | Weigh all chicks and feed, then sacrifice one pen from each treatment, necropsy to determine lesion scores. |
| 0–28 | Birds checked daily to ensure proper management. |

Statistical comparisons were made using a one-way analysis of variance as described above. Results of this experiment are presented in Table 9. Pre-challenge, all chicks grew at a statistically similar rate and significant differences (P≦5%) in mortality rates, as well as feed conversion ratios were not found. These results suggest that the sporozoite type vaccine did not affect growth, development, or livability of the chicks during the early development period.

During the challenge period, significant (P≦5%) differences among the treatments were found. The positive controls gained significantly less weight than all the other groups. It is interesting to note that the other three groups were not statistically different. Lesion scores in the negative control groups were significantly lower than in all other groups and IYS and trickle treatments, although not significantly different from each other, were significantly lower than positive controls.

These results indicate that the sporozoite vaccine protected chicks equally as well as the trickle treatment with oocysts, and even better than the oocyst vaccine. These results suggest that when sporozoites are used to vaccinate day old chicks by the intrayolk sac route, immunity develops by as early as 3 weeks to protect broilers from challenge with live oocysts. This protection was comparable to that afforded by early trickle vaccination with 200 oocysts. These results suggest that IYS vaccination with sporozoites is a feasible and commercially advantageous procedure.

TABLE 9

Results of IYS sporozoite vaccination of chicks under field conditions

| Parameter | Treatment Neg. Con | Pos. Con | IYS | Trickle |
|---|---|---|---|---|
| Gain (g) (0–3 wks)[1] | 377[a] | 432[a] | 402[a] | 401[a] |
| Gain (g) (3–4 wks)[2] | 303[a] | 231[b] | 291[a] | 313[a] |
| Mort (%) (0–3 wks)[3] | 3.0[a] | 5.0[a] | 10.0[a] | 9.0[a] |
| Mort (%) (3–4 wks)[4] | 0.0[a] | 6.0[a] | 1.0[a] | 0.0[a] |
| FC (0–3 wks)[4] | 1.95[a] | 1.85[a] | 2.01[a] | 1.93[a] |
| FC (3–4 wks)[6] | 1.88[a] | 3.09[a] | 2.17[a] | 1.98[a] |
| Lesion Scores (3–4 wks)[7] | 0.1[c] | 3.7[a] | 2.4[b] | 1.9[b] |

[a–c]Means in a row, i.e. for each parameter, which possess different superscripts differ significantly at Probability of 5%.
[1–2]Gain (0–3 weeks) is gain before challenge; gain (3–4 weeks) is gain during the week immediately following challenge.
[3–4]Mort (0–3 weeks) is percentage cumulative mortality during pre-challenge; and Mort (3–4 weeks) is percentage cumulative mortality during the week immediately following challenge.
[5–6]FC (0–3 weeks) is feed conversion ratio during pre-challenge and FC (3–4 weeks) is feed conversion ratio during the week immediately post-challenge.
[7]Lesion scores 3–4 weeks is mean lesion score during the week immediately post-challenge.

The above Examples are intended to illustrate further the practice of the invention and are not intended to limit the scope of the invention in any way.

What is claimed is:

1. A method for the delivery of medicaments to newly hatched, domestically raised poultry, comprising the steps of:

(a) sequentially and individually orienting the poultry in a manner that facilitates access to the skin covering the residual yolk sac of each individual chick, and (b) injecting an effective amount of the medicament thorough the skin and into the yolk sac of each oriented chick.

2. The method of claim 1 wherein the medicament is selected from the group consisting of vaccines, nutrients, antibiotics, probiotics, growth stimulators and sexual function modifiers.

3. The method of claim 2 wherein the medicament comprises a vaccine.

4. The method of claim 3 wherein the medicament comprises a vaccine for coccidiosis.

5. The method of claim 4 wherein the vaccine is selected from the group consisting of oocysts and sporozoites of the genus Eimeria.

6. The method of claim 2 where in the medicament comprises an antibiotic selected from the group consisting of oxytetracycline, chlortetracycline, spectinomycin, cephalosporin, gentamicin, lincomycin, and quinolones.

7. The method of claim 2 wherein the medicament comprises a nutrient selected from the group consisting of vitamins, minerals, amino acids, sugars, and fatty acids.

8. The method of claim 2 wherein the medicament comprises a growth promoter selected from the group consisting of growth hormone, growth hormone releasing hormone, insulin-like growth factors I and II, avian interleukins (e.g., $aIl_2$), nerve growth factors, thyroxine releasing hormone, thyroxine stimulating hormone, monoiodotyrosine, diiodotyrosine, triiodothyronine, thyroxine and corticosterone.

9. The method of claim 2 wherein the medicament comprises a sexual function modifier selected from the group consisting medullarin inhibitory substance, 17-beta-estradiol, estrone, estrogen, progesterone, testosterone, epiandrostenedione, gonadotropin releasing hormone, follicle stimulating hormone, luteinizing hormone, and prolactin.

10. The method of claim 1 wherein the medicament is useful for the treatment of a poultry disease selected from the group consisting of fowl cholera, Colibacillosis, fowl pox, infectious bronchitis, infectious bursal disease, laryngotracheitis, leukosis complex, Marek's disease, lymphoid leukosis, reticuloendotheliosis, lymphoproliferative disease, Newcastle Disease, and viral arthritis.

11. The method of claim 1 wherein the injection is performed within about 24 hours after the chick is hatched.

* * * * *